United States Patent [19]

Harding et al.

[11] 4,375,695
[45] Mar. 1, 1983

[54] DEVICE FOR DETERMINING THE DENSITY DISTRIBUTION IN AN OBJECT

[75] Inventors: Geoffrey Harding, Rellingen; Wolfgang Wagner, Hamburg, both of Fed. Rep. of Germany

[73] Assignee: U.S. Philips Corporation, New York, N.Y.

[21] Appl. No.: 198,740

[22] Filed: Oct. 20, 1980

[30] Foreign Application Priority Data

Nov. 2, 1979 [DE] Fed. Rep. of Germany ....... 2944147

[51] Int. Cl.³ .......................... A61B 6/00; G01T 1/29
[52] U.S. Cl. ..................................... 378/006; 378/010
[58] Field of Search ................... 250/445 T; 378/006, 378/010

[56] References Cited

U.S. PATENT DOCUMENTS

3,106,640 10/1963 Oldendorf ...................... 250/445 T
4,277,686 7/1981 Harding .......................... 250/445 T

*Primary Examiner*—Alfred E. Smith
*Assistant Examiner*—T. N. Grigsby
*Attorney, Agent, or Firm*—Jack E. Haken

[57] ABSTRACT

In a device for determining the density distribution on a straight line by means of a narrow penetrating beam, the measuring accuracy for the center of an object to be examined is increased in that the primary beam is not only displaced perpendicularly to its direction, but is also rotated around a point in this center. To this end, a radiation source and a detector device are mounted on a supporting device which can rotate the path of the primary beam around a central point, preferably the center of the object, around an axis which intersects the path of the primary beam at right angles.

9 Claims, 8 Drawing Figures

DEVICE FOR DETERMINING THE DENSITY DISTRIBUTION IN AN OBJECT

The invention relates to a device for determining the density distribution in an object, comprising at least one radiation source for generating a narrow primary beam which irradiates the object, a detector device which is arranged adjacent the primary beam for detecting scattered radiation produced by the primary beam, a diaphragm device which is arranged between the detector device and the object and which is shaped so that the detector device measures a set of scattered radiation values from the path of the primary beam through the object, and a drive device for the displacement of the path of the primary beam through the object.

BACKGROUND OF THE INVENTION

A device of this kind is known from German Offenlegungsschrift No. 27 13 581. The diaphragm device thereof comprises a slit-shaped aperture, the principal dimension of which extends in a direction approximately perpendicularly to the primary beam. The detector device comprises a series of detectors which are arranged behind the diaphragm device. Each detector can be struck only by the scattered radiation which is generated in a given part of the primary beam, so that a given part of the object is associated with each detector. The detectors together measure the path of the primary beam in the object. The invention can also be used in devices where the diaphragm device is a multi-channel diaphragm as described in German Offenlegungsschrift No. 26 55 230. Instead of a detector device consisting of many separate detectors, use can also be made of a different type of location-sensitive detection device, for example, a gamma camera or an X-ray image intensifier. It is important that an unambiguous spatial relationship exists between parts of the path of the primary beam on the one side and separately readable parts of the detector device on the other side.

For a given path of the primary beam through the object to be examined, only the scattered radiation in this path can be measured. Therefore, it is necessary to change the path of the primary beam with respect to the object in order to measure the scattered radiation in a slice of the object. In all known devices this is done transversely to the primary beam.

SUMMARY OF THE INVENTION

The invention is based on the following considerations: in this type of device, both the primary radiation and the scattered radiation produced in the body are attenuated by photo-absorption or by Compton dispersion. This attenuation increases with the distance travelled by the primary beam to the point wherefrom the scattered beam departs, and with the distance travelled through the body by the scattered radiation. In general, therefore, the intensity of the scattered radiation which originates from the centre of a body is lowest. However, the lower the radiation intensity measured by the detector device, the greater the inaccuracy of the measured values will be. Thus the density distribution in the centre of the body to be examined can only be reconstructed comparatively inaccurately. However, the zones which are of interest for the diagnosis are often situated in the centre of the body.

The intensity of the primary beam can be increased in order to increase the accuracy. However, this increases the radiation dose applied to the patient without the accuracy being substantially increased in the outer zones of the body.

The accuracy of the measurements of the central zone can also be improved by making the primary beam pass through the centre in different directions, without increasing its intensity, and by summing the measuring values obtained in the overlapping zone of the beams. The sum value thus formed is multiplied by a factor which is proportional to the coverage of density in this zone, so that a mean value of the measuring values in this zone is determined. The dose in the centre of the body is thus increased but the dose in the outer zones of the body is not substantially increased.

In view of these considerations, the invention has for its object to construct a device of the described kind so that the centre of the object is irradiated more often by the primary beam than the outer zones.

This object is achieved in that the radiation source and the diaphragm device are mounted on a supporting device which leaves an object space free and which is rotatable around an axis which intersects the path of the primary beam and which is transverse thereto.

In accordance with the invention, a circular examination zone is scanned by means of a primary beam which is directed onto the centre thereof. During the rotation of the supporting body, the radiation source is rotated along an arc of a circle around the centre of the examination zone so that, ignoring the attenuation of the radiation in the object, a concentration is obtained which increases in the direction of the centre. If the intensity attenuation is taken into acount, an approximately uniform concentration is thus obtained. Because the accuracy with which a scattered radiation coefficient can be calculated is dependent on the measured number of photons dispersed in this point, the device in accordance with the invention offers a substantially higher image quality for the centre of the object than the known devices where displacement always takes place perpendicularly to the direction of the primary beam.

It is to be noted that the application No. P 28 31 311 discloses a device for determining internal body structures by means of scattered radiation which corresponds to the so-called transmission computer tomography apparatus, however, therein the scattered radiation produced along the stopped primary beam is also measured by means of two hollow cylindrical detectors which are arranged one on each side of the examination plane and which enclose the body being examined. However, the hollow cylindrical detectors can only measure the scattered radiation generated by the primary beam over the entire examination zone, and cannot distinguish the scattered radiation which is generated at individual points struck by the primary beam. Moreover, therein the primary beam is displaced perpendicularly to its direction and the device is rotated through a small angular increment after the complete examination zone has thus been scanned. Ignoring the intensity attenuation by the body being examined, the concentration of primary radiation in the examination zone is homogeneous, which is contrary to the invention where the concentration is higher in the centre.

In a further embodiment in accordance with the invention, the detector device is also mounted on the supporting device. In all positions of the supporting device, each element of the detector device measures only the scattered radiation originating from a given zone of the primary beam. Each detector thus measures the scattered radiation in an arc of a circle around the axis of rotation.

In a further embodiment in accordance with the invention, the detector device forms a stationary arc of a circle which is concentric to the axis of rotation of the supporting device. Between this embodiment and the previously described embodiment there is a difference which is analogous to the difference between a transmission computer tomography apparatus of the fourth generation and one of the third generation. The detector device in general requires a larger number of detector elements than the previously described embodiment. Therefore, the assignment of a detector element to the primary beam changes as the supporting device is rotated, so that the scattered radiation generated in a given zone of the primary beam is each time measured by a different element of the detector device in each rotary position of the supporting device. Differences in sensitivity of the various elements of the detector device, therefore, have only a small effect on the reconstruction of the density distribution. Ring-shaped artefacts which are liable to occur in the former embodiment when the sensitivity of a detector element deviates from that of the other detector elements are not intensified.

The accuracy and the response sensitivity can be further increased by arranging different diaphragm devices on both sides of the primary beam, each element of the detector device then measuring the scattered radiation generated in a given zone of the primary beam through said diaphragm devices. For example, when two diaphragm devices are arranged one on each side of the primary beam, the scattered radiation produced in a given zone of the primary beam is measured by a total of four elements of the detector device. The four measuring values are added in order to form a signal which corresponds to the density in this zone.

As is known, devices of the described kind, including the device in accordance with the invention, enable a simpler reconstruction of the density distribution in the slice than so-called transmission computer tomography apparatus, because each detector already measures the density generated in a given point in a given zone, rather than the line integral of the density over the relevant radiation path, as in transmission computer tomography apparatus. On the other hand, the reconstructed density distribution gives only a qualitative result if neither the attenuation of the primary beam up to the point in which the scattered radiation is generated nor the attenuation of the scattered radiation on its way to the relevant detector element is taken into account. This can in principle be realized by means of a suitable computer program in which given assumptions as regards the mean density and the dimensions of the object to be examined are made. The density distributions thus obtained can be further improved by suitable iteration methods, but they generally cannot be accurate in view of these assumptions.

A more accurate determination of the density distribution is possible in a further embodiment in accordance with the invention which comprises an X-ray source whose radiation can be stopped by a collimator so that it passes through the total examination zone and is measured by a detector device which is arranged behind the examination zone. Therein, the X-ray source forms part of a computer tomography apparatus of the third or fourth generation (depending on whether the detector device is moved or not), which is capable of determining the absorption distribution in the examination plane by means of a computer. The additional costs are low, because the detector device and the mechanism for rotating the source around the examination zone are already present.

The attenuation can be calculated for each individual measuring value from the absorption density distribution thus obtained, because the paths of the primary beam up to the scatter point and from the scatter point to the relevant detector element are fixed. It is merely necessary to add the attenuation coefficients obtained along these paths, so that the total attenuation can be calculated. The values measured by the individual detector elements must then be weighted by a weighting factor which is proportional to the attenuation factor calculated for the total beam path. The dose applied to the patient during such a determination of the absorption distribution can be substantially smaller than in transmission computer tomography apparatus. The absorption coefficients measured in the individual points are less accurate however these reconstruction errors do not exert their full effect because the attenuation coefficients of many points have to be added for the determination of the attenuation of a primary or scattered beam and errors are at least partly eliminated by averaging. Moreover, the X-ray source can efficiently operate with the same high voltage (for example, 350 kV) such as during the determination of the density distribution, so that the dose is also reduced.

However, it is also possible to operate the X-ray source with the same tube voltage and the same intensity as customarily used for transmission computer tomography in order to obtain the absorption distribution. On the basis of the absorption distribution thus obtained, the density distribution can be accurately reconstructed. The scatter contributions to the transmission compuer tomogram (the absorption in an individual point of the transmission computer tomogram is composed of an attenuation component by photoabsorption and an attenuation component by scattering) can be determined using the density distributions and subtracted from the values obtained; this results in the photo-absorption. At the end of these calculations, two density distributions are then obtained: on the one hand the density distribution due to radiation scattering in the examination zone and on the other hand the photoabsorption therein. The radiologist can derive extra information therefrom.

The invention will be described in detail hereinafter with reference to the accompanying diagrammatic drawing.

Figure 1:
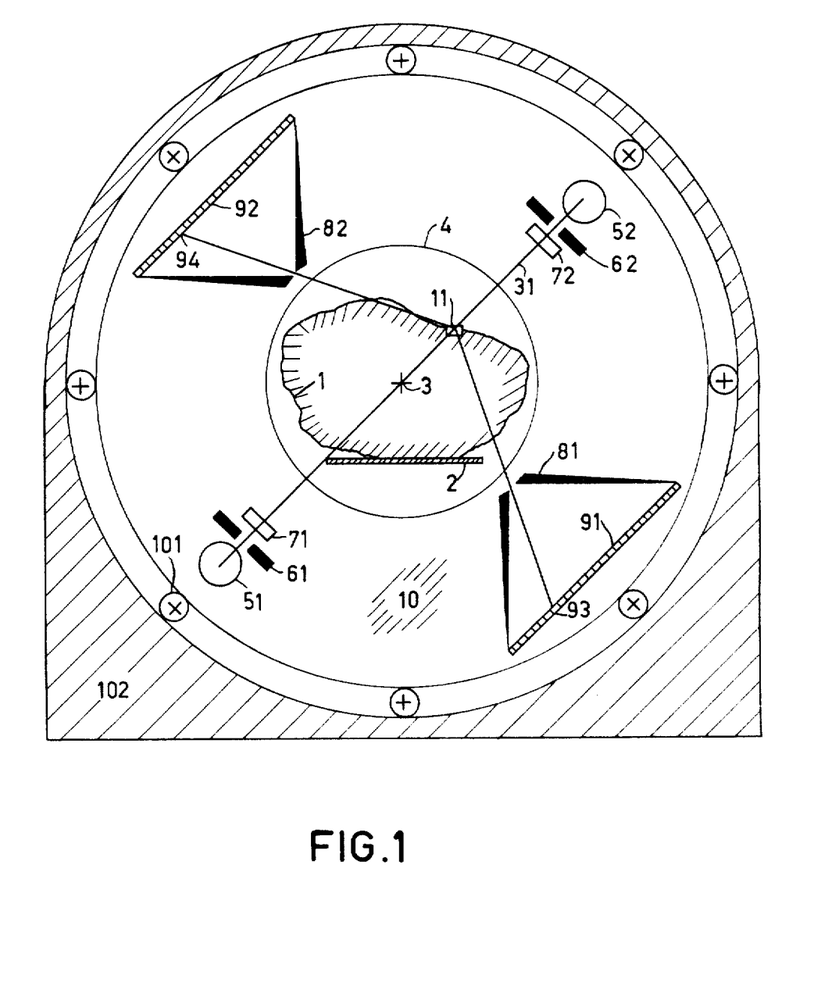
FIG. 1 shows first embodiment in accordance with the invention, comprising two oppositely arranged X-ray sources and detector devices mounted on the supporting device.

The reference numeral 102 in FIG. 1 denotes a stationary housing in which a supporting device 10 is journalled to be rotatable around an axis 3 by way of roller bearings 101. The drive units for rotating the supporting device 10 are not shown. The supporting device comprises an aperture 4 which defines the examination zone within which the scattered radiation can be determined. On an examination table 2 inside this examination zone there is arranged the patient body 1. The density distribution is to be determined in a given slice of the body. To this end X-ray sources 51 and 52 are disposed on either side of the examination zone (which is concentrically situated with respect to the axis 3) collimators 61 and 62 which stop registering primary beams 31 which intersect the axis of rotation are disposed in front of the sources 51 and 52.

Transmission detectors 71, 72 which are provided with holes (not shown) in order to allow unobstructed passage of the primary beam from its relevant radiation source are disposed in front of the collimators, while the primary beam from the oppositely situated radiation source, attenuated by the examination zone, can be detected as a result of the dispersion inside the body. Using these detectors, any assumptions concerning the attenuation inside the body can be corrected as described in German Offenlegungsschrift No. 27 13 581.

Two detector devices 91 and 92 which consist of a large number of adjacently arranged detector elements whose largest dimension extends in the direction perpendicular to the plane of the drawing are disposed on either side of the primary beam 31 and outside the examination zone 4 on the rotatable supporting device 10, as described in German Offenlegungsschrift No. 27 13 581. Between each of the two detector devices 91 and 92 and the examination zone 4 slit-like diaphragms 81, 82 are disposed which provide an unambiguous spatial assignment of a point or zone, for example, the zone 11, of the primary beam to the detector device 91, 92, so that the scattered radiation generated in this point 11 of the primary beam is measured by the detector elements which are present at locations 93 and 94. The scattered radiation generated at other locations in the primary beam within the examination zone 4 is measured by other elements of the detector device 91, 92, for example, as described in German Offenlegungsschrift No. 27 13 581.

In the latter device the primary beam is displaced perpendicularly to its direction with respect to the examination zone in order to determine the density distribution in a slice; however, in the present case the complete slice to be examined is covered in that the supporting device 10 is first rotated through a small angular increment, after which the two detector devices record new sets of measuring values, after which a further rotation through a small angular increment takes place etc. until the device has been rotated through a total angle of 180°. The angular increments are chosen so that the complete contour is also completely covered by the various primary beams. The primary beam remains directed onto the axis of rotation 3.

It is alternatively possible to use only a single detector and diaphragm device; however, the probability of detection is then lower if the detector surfaces are not increased. Instead of using two X-ray sources, it is alternatively possible to use only a single source. However, for a complete measurement a rotation of the supporting device through 360° is then required in order to expose each point on the contour of the examination zone 4 once to the unattenuated primary beam.

Figure 2:
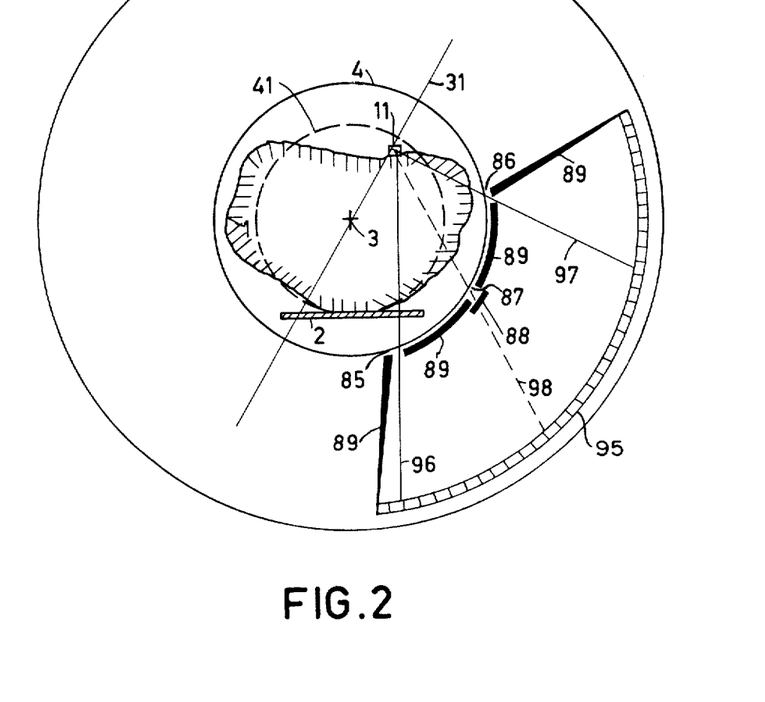
FIG. 2 shows a similar device, which, however, offers a better probability of detection of scattered radiation.

FIG. 2 shows a part of a further embodiment in which two detector systems are arranged on each side of the primary beam 31. For the sake of simplicity, the two detector systems to the left of the primary beam 31 and the two X-ray sources generating the primary beam are not shown. The two detector devices are advantageously combined to form a single detector device 95. A diaphragm device 89, comprising two slits 85 and 86, is arranged between each detector device and the examination zone. The slits are proportioned and situated so that the lower part of the elements of the detector device can be struck by scattered radiation which is generated in the primary beam 31 and which passes through the slit 85, whilst the upper part of the elements of the detector device can be struck by scattered radiation which is generated in the primary beam within the examination zone and which passes through the slit 86. No element of the detector device can then measure radiation which passes through the slit 86 as well as through the slit 85 and which originates from the primary beam within the examination zone 4.

This embodiment of the detector and diaphragm device increases the probability of detection, thus improving the reconstruction accuracy because the scattered radiation from each point on the primary beam 31 can be measured by two different detector elements, as is shown in FIG. 2 for the scattered beams 96 and 97 which originate from the point 11 on the primary beam 31 and which pass through the slits 85 and 86. Moreover, the two diaphragm and detector devices complement each other, i.e. the scattered radiation originating from the lower left half of the primary beam in FIG. 2 is measured better by the detector elements associated with the slit 85, whilst scattered radiation from the upper right half of the primary beam 31 is measured better by the elements associated with the slit 86. This is because the scattered radiation produced in the lower left half of the primary beam 31 is attenuated less when it passes through the slit 85, whilst the scattered radiation produced in the upper right half of the primary beam is attenuated less when it passes through the upper slit 86.

The diaphragm device 89 in FIG. 2 comprises a further slit 87 which is covered by a shield 88 during normal operation. When the cross-section of the body 1 is so small that it is situated within the circle 41 which is concentric with respect to the axis of rotation 3 and whose diameter is smaller than the diameter of the examination zone 4, the shield 88 can be moved out of the beam path by means of a drive unit (not shown). A further scattered radiation path 89 is then opened, thus increasing the probability of detection of scattered radiation and hence the measuring speed. The circle 41 is proportioned so that each element of the detector device can "see" only one point on the primary beam within the circle 41 through the slits 85, 86 and 87, so that disturbing superposition of scattered radiation which can reach a detector element via at least two different scattered radiation beam paths, is precluded.

Figure 3A:
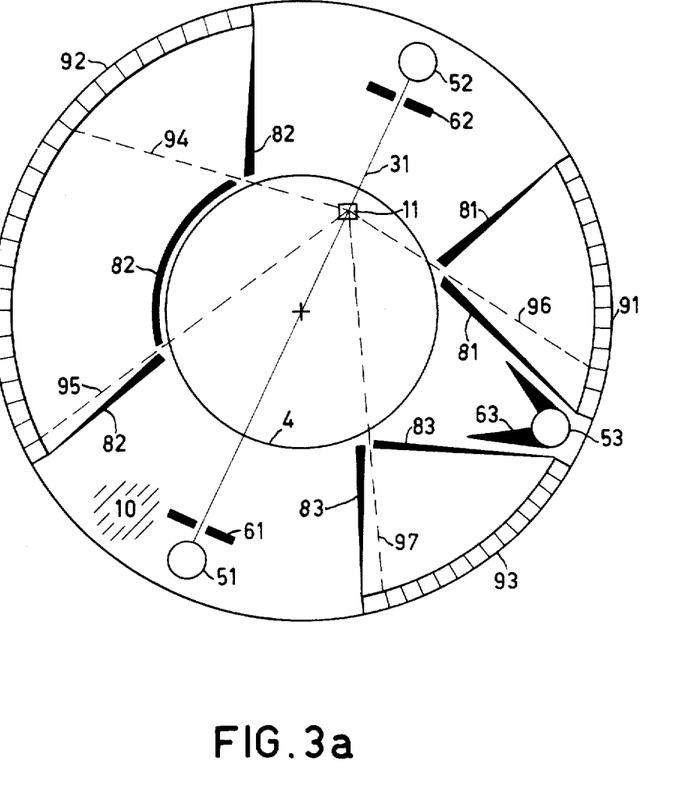
FIG. 3a shows a device whereby at the same time a transmission computer tomogram can be made.

FIG. 3a also shows a device comprising two X-ray sources 51 and 52 which are arranged on the supporting device 10 with collimators 61 and 62 which are arranged in front of the sources and wherethrough the primary beam 31 passes. Two detector devices are arranged on each side of the primary beam. However, whilst on the left half the elements of the two detector devices 92 adjoin directly and are covered by a common diaphragm device 82 comprising two slits, the detector devices 91 and 93 are separated on the right side and each detector device comprises a slit diaphragm device 81, 83. For example, the scattered radiation produced in the point 11 reaches, along the lines 94, 95, 96 and 97, an element in the different detector devices. Between the two detectors and diaphragm devices 81, 91 and 83, 93 there is arranged an X-ray source 53, i.e. opposite the detector device 92. In front of the source there is provided a collimator 63 which is shaped so that the radiation generated by the source 53 passes through the examination zone 4 in the same plane as the primary beam 31.

Figure 3B:
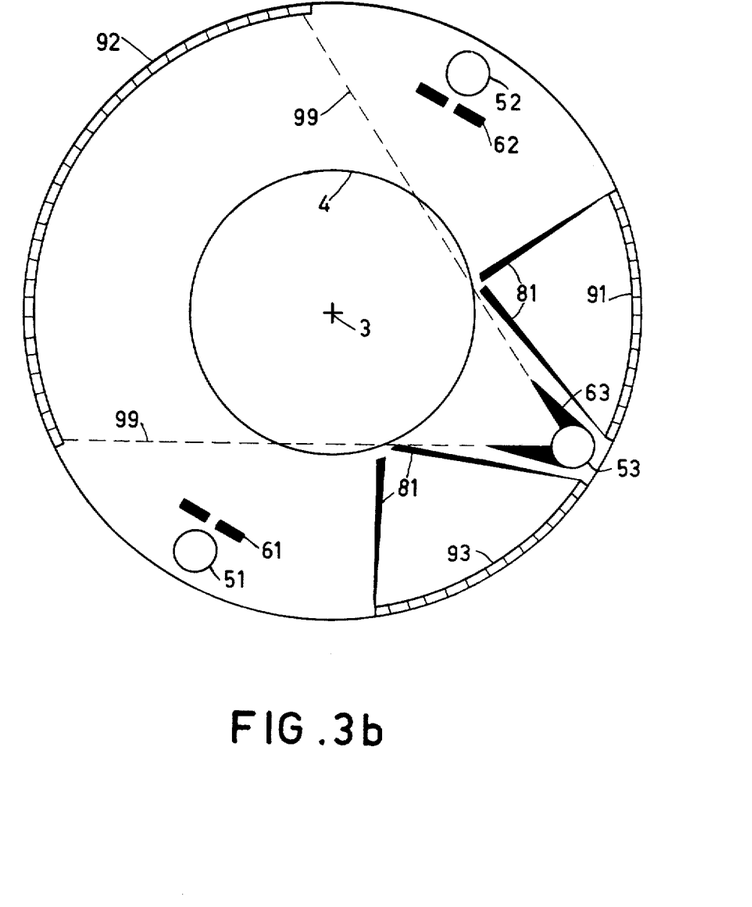
FIG. 3b shows this device during the measurement required for the transmission computer tomogram.

FIG. 3a shows the device in an examination phase where the primary beam 31 passes through the examination zone 4 in order to determine the density distribution, and FIG. 3b shows the phase in which the X-rays generated by the source 53 irradiate the complete examination zone between the rays 99 in order to determine the attenuation distribution within the examination zone 4. In this phase, a drive and displacement device (not shown) displaces the slit diaphragm device 82 perpendicularly to the plane of examination, so that the elements of the detector device 92 can measure the radiation beam of the radiation source 53.

The two examination phases shown in the FIGS. 3a and 3b may be performed in direct succession, the tube voltage which is initially applied to the X-ray sources 51 and 53 for at least one half revolution, subsequently being switched over to the X-ray source 53 until the attenuation distribution within the examination zone 4 has been completely measured by means of the detector device.

It will be clear that the cost of the additional execution of transmission computer tomography are comparatively low, because the detector device 92 for measuring the transmission measuring values is already required for the scattered radiation measurement and so is the rotatable supporting device.

Figure 4:
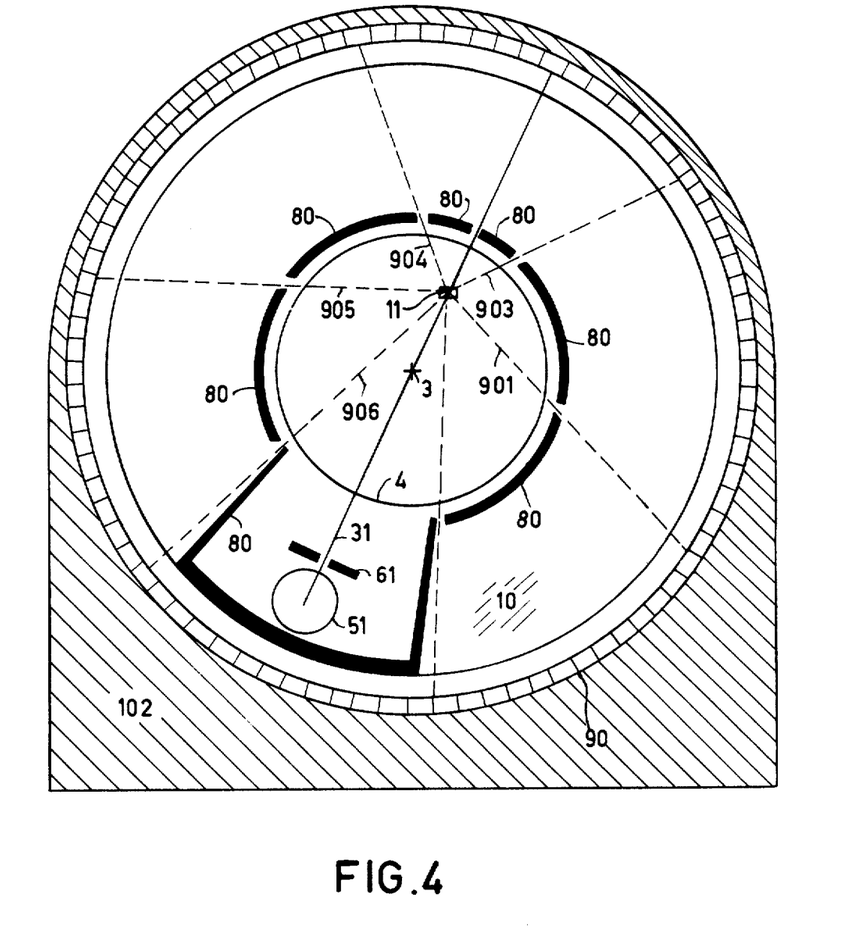
FIG. 4 shows a device in which the elements of the detector device are arranged to be stationary on an arc of a circle around the axis of rotation.

FIG. 4 shows an embodiment which differs from the embodiment described thus far in that the detector device is connected to the housing 102 and is constructed as a stationary circle of separate detector elements which concentrically encloses the axis of rotation 3 and the supporting device 10. Only the X-ray source 51 with the collimator 61 for the formation of the primary beam 31 and the diaphragm device 80, comprising a total of seven slits, are arranged on the supporting device 10 which in this embodiment, comprising only one X-ray source, has to be rotated through 360°. The primary beam 31 passes through a slit which is situated diametrically opposite the X-ray source 52, so that the element each time present behind this slit can measure the attenuation of the primary beam 31. The six other slits in the diaphragm device 80 are distributed on both sides of the primary beam so that in each angular position of the supporting device 10, each element of the detector device can be reached through a slit only by scattered radiation which is generated within the examination zone 4 and in the primary beam 31. FIG. 4 again shows the six beam paths 901 to 906 along which the scattered radiation generated in the point 11 reaches six different elements of the detector device.

The embodiment shown in FIG. 4 usually requires more detector elements than the previously described embodiments, but these elements need not be moved. Moreover, a detector element is not permanently assigned to an arc of a circle around the axis of rotation 3; this means on the one hand that ring-like artifacts which are liable to occur in the described devices when the sensitivity of a detector element deviates from that of the other elements, cannot occur; on the other hand, it also means that for the determination of the density distribution on an arc of a circle around the axis of rotation 3, the measuring values of a large number of different detector elements must be taken into account. Moreover, the journalling elements for the supporting device 10 (not shown in FIG. 4) must be arranged so that they do not shield the scattered radiation paths to the detector elements.

Figure 5A:
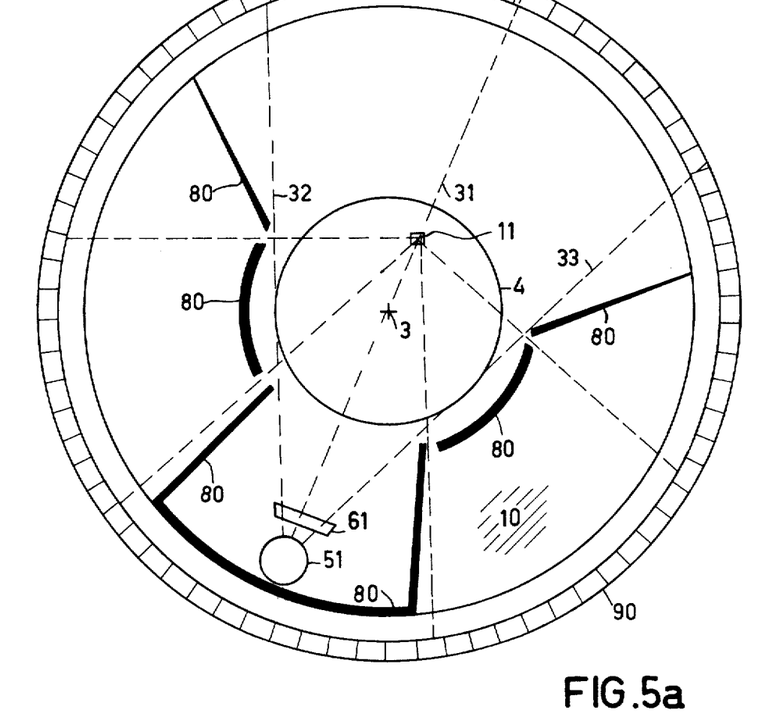
FIGS. 5a and 5b show a corresponding device which, however, is also suitable for making transmission computer tomograms.

FIG. 5a shows an embodiment comprising stationary detector elements which also enables measurement of transmission measuring values. Like in FIG. 4, the detector device which consists of a stationary ring of detector elements which is concentric to the axis of rotation 3 is mounted on the supporting frame of the device (not shown). Like in FIG. 2, the diaphragm device 80 is shaped so that the radiation beam which covers the entire examination zone 4 between the extreme rays 32 and 33 is not influenced by the diaphragm device 80.

Figure 5B:
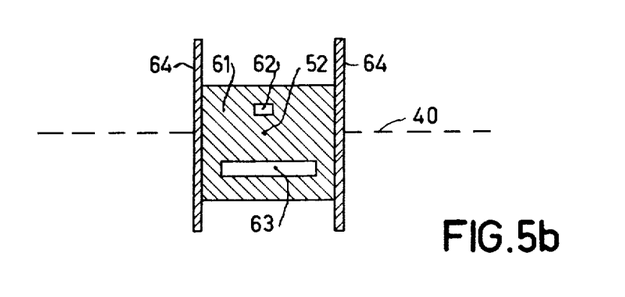

In front of the radiation source 51 there is arranged a collimator plate which is displaceable perpendicularly to the plane of the drawing and which comprises two apertures 62 and 63 which are situated perpendicularly one above the other (see FIG. 5b). When the opening aperture 62 is slid into the examination plane 40, a narrow collimated primary beam 31 is stopped and the density distribution can be measured. However, when the aperture 63 is slid into the examination plane 40, a fan-shaped radiation beam with the extreme rays 32 and 33 is stopped and transmission measurements can be performed. The measurements can be consecutively performed, i.e. during a rotation through 360° first the density distribution is determined and then the attenuation distribution, or vice versa. However, during operation, that is to say during the rotation of the supporting device 10, it is alternatively possible to slide the diaphragm 61 quickly to and fro on the stationary rails 64, extending perpendicularly to the plane of the drawing of FIG. 5a, so that the primary beam 31 and the radiation beam with the outer rays 32 and 33 are alternately emitted. It is thus ensured that the scattered radiation and the transmission radiation are measured in neighbouring angular positions of the supporting device 10 without substantial delay.

In the device shown in FIG. 5a, the additional cost for executing the computer tomography are only for the collimator plate 61 which is displaceable perpendicularly to the plane of examination.

Figure 6:
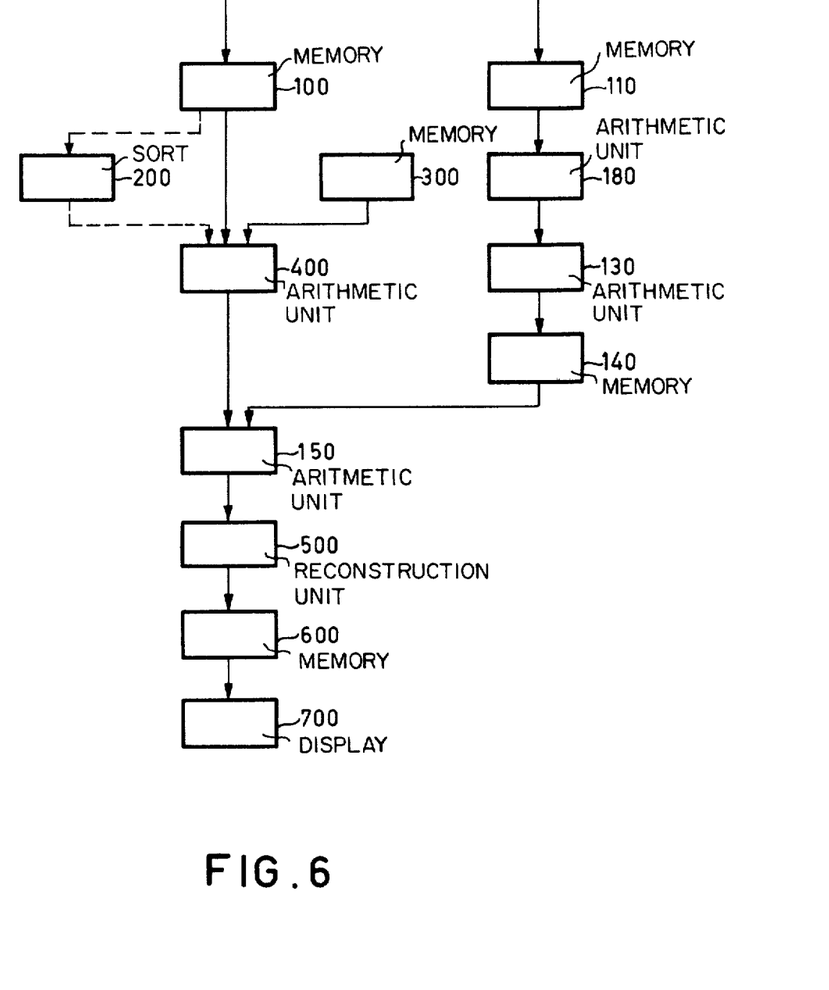
FIG. 6 shows a device for reconstructing the density distribution on the basis of the measuring values obtained.

FIG. 6 shows a device for reconstructing the density distribution from measuring values obtained by means of a device as shown in the FIGS. 3a, 3b or 5a, 5b, comprising a memory 100 whereto the scattered radiation measuring values are applied. These measuring values are weighted with different weighting factors in the arithmetic unit 400. It is thus taken into account that for a point in the centre of the examination zone a substantially larger number of measuring values is present than for a point outside the centre, so that the measuring values for a point in the centre must be weighted with a correspondingly lower factor before or after the summing.

For example, if it is assumed that the number z of scanning directions and the dimensions of the primary beam are selected so that the primary beams cover each location on the periphery of the examination zone 4 exactly once, and if it is also assumed that the density in a polar coordinate system is to be reconstructed in points which are situated on straight lines through the centre whose angular positions correspond to those of the primary beam with respect to the examination zone, the distance a between the centres of two adjacent points on a straight line corresponding to the width of the primary beam, the weighting factors are formed as follows:

The measuring values for the point in the centre, or the sum thereof, are weighted by a weighting factor $1/Z$, because the primary beam passes through this point in all z angular positions. For a point outside the centre, the measuring values, or the sum thereof, are weighted by a factor $n/N$, N being $z/2\pi$ and n being an integer value which indicates how many times the distance between the centre 3 of the examination zone and the centre of the relevant point is larger than the distance a between two adjacent points.

The weighting factor distribution is thus formed for a polar coordinate system. However, if desired, after application of known transformation rules, the weighting factors for points in a cartesian coordinate system can be calculated therefrom.

Simultaneously with this weighting factor, other weighting factors which are dependent of the geometry of the device, for example, the angular dependency of the scattered radiation, and the different detector sensitivities can be taken into account. The resultant weighting factors are stored in the memory 300.

The reference numeral 200 denotes a sorting unit which, in the case of stationary detectors (FIG. 5a), sorts the measuring values of permanently stored coordinate transformations so as if the measuring values were measured by rotating detector elements (like in FIG. 3a). In a further arithmetic unit 150, the values thus weighted are weighted by a factor which corresponds to the attenuation of the radiation by the body. The higher the attenuation, the larger the weighting factor will be.

These values are derived from the transmission computer tomogram. To this end, the transmission measuring values are stored for the time being in the memory 110 and the attenuation density distribution in the examination zone is reconstructed therefrom in the arithmetic unit 180. For each separate point in the examination zone it can be calculated to what extent the primary radiation has been attenuated on its way to this point and how much the scattered radiation has been attenuated in order to reach a given detector element from this point. The attenuation coefficient is the line integral over the attenuation coefficients along the primary beam as far as the relevant point and further over the relevant scattered radiation path to the detector element. These values are calculated in one point in an arithmetic unit 130 and are intermediately stored in the memory 140 and need for the weighting of the values, supplied by the arithmetic unit 400, in the arithmetic unit 150. From the values supplied by the arithmetic unit 150, the density distribution is calculated in the reconstruction unit 500, each element of the detector device, assumed to have rotated along, being associated with a concentric circle in the reconstruction plane, and each measuring value on a point of this circle being transferred under a pole angle which corresponds to the angle of rotation with which this measuring value has been obtained. After completion of these calculations, the image is stored in the memory 600 and displayed on a display apparatus 700.

The weighting factors corresponding to the relevant attenuation cannot only be determined by measurement by means of a transmission computer tomogram, but also by way of attenuation measurements which are performed on a suitable phantom. For different body cross-sections of patients of different size, use must be made of different phantoms whereto each time a set of weighting factors must be assigned in the memory 140. This enables only an approximate determination of the relevant weighting factor, which is better as the selected phantom cross-section corresponds better to the body cross-section examined.

It is in principle also possible to determine the attenuation of the scattered radiation, or the weighting factors taking into account this attenuation, by calculation. To this end, first the contour of the body slice to be examined is determined by comparing each measuring value with a threshold value which corresponds approximately to the scatter coefficient of water or which is slightly lower. When a measuring value is lower than the threshold value, it is assigned to the part of the examination zone situated outside the body (air); if it is larger, it is assigned to the body slice.

The slice of the body thus obtained is first assigned a homogeneous density distribution, this density being assumed to be equal to that of water. This is a suitable approximation of the actual conditions, because a human body largely consists of water. The attenuation of the primary beam occurring for the indicated density distribution is calculated for the individual scanning directions and is compared with the attenuation values resulting from the measuring values from the elements 71 and 72 (FIG. 1). The difference is used for correcting the assumed density distribution.

From the density distribution thus corrected, the attenuation of the beam along the primary beam path to the scatter point (for example, 11, FIG. 2) and therefrom to the detector via the scattered beam path (for example, 97) is determined. This calculation is successively performed for all scanning directions or angular positions and all detector positions, and the results are stored. Using the beam attenuation values stored, being each time the reciprocal values of the weighting factors, the measured scattered radiation measuring values are corrected. Therefrom a corrected density distribution can be determined.

The measured density distribution can be further improved by comparing the density values determined for the individual points again with the scatter coefficient of water in order to determine not only the contour of the body, like in the previously described comparison cycle, but also areas inside the body whose scatter coefficient deviates substantially from that of water (for example, air or bone). Subsequently, the described cycle is completed again; if necessary, it may be repeated again.

What is claimed is:

1. In a device for determining the density distribution in an object which comprises:

radiation source means for generating a narrow primary beam which irradiates the object;

detector means arranged adjacent the primary beam for detecting scattered radiation produced in the object by the primary beam;

diaphragm means arranged between the object and the detector means which function to collimate the scattered radiation so that the detector means measure a set of scattered radiation values from the path of the primary beam in the object; and drive means for displacing the path of the primary beam through the object;

the improvement wherein the device further comprises:

support means which define a free space around the object and which are rotatable about an axis which intersects the path of the primary beam and is directed transverse thereto;

wherein the drive means function to rotate the support means about the axis; and wherein the radiation source means and the diaphragm means are mounted on and rotate with the support means.

2. A device as claimed in claim 1, wherein the detector means are mounted on and rotate with the support means.

3. A device as claimed in claim 1, wherein the detector means are stationary and form an arc of a circle which is concentric with the axis.

4. A device as claimed in any one of the preceeding claims 1-3, comprising:

a first plurality of diaphragm means arranged on first side of the primary beam and a second plurality of diaphragm means arranged on a second side of the primary beam which is opposite the first side;

wherein the detector means comprise a plurality of detector elements; and wherein each of the diaphragm means functions to collimate scattered radiation so that, at each rotational position of the support means, scattered radiation from a given zone of the primary beam passes through each of the diaphragm means to an associated element of the detector means.

5. A device as claimed in claim 4, wherein the radiation source comprises an x-ray source; and further comprising:

a first collimator associated with the radiation source, and an additional radiation detector which is disposed and functions to measure the intensity of x-rays which have passed from the x-ray source through both the first collimator and the object.

6. A device as claimed in claim 5, further comprising:

a second collimator disposed between the radiation source and the object and means for displacing the second collimator perpendicular to the plane of examination, the second collimator defining two apertures and functioning so that when the second collimator is displaced to a first position a first aperture defines the narrow primary beam and when the second collimator is displaced to a second position the second aperture defines a wide radiation beam which irradiates an entire examination plane in the object.

7. A device as claimed in claim 1, 2 or 3, wherein the radiation source comprises an x-ray source; and further comprising:

a first collimator associated with the radiation source; and an additional radiation detector which is disposed and functions to measure the intensity of x-rays which have passed from the x-ray source through both the first collimator and the object.

8. A device as claimed in claim 7, further comprising:

a second collimator disposed between the radiation source and the object and means for displacing the second collimator perpendicular to the plane of examination, the second collimator defining two apertures and functioning so that when the second collimator is displaced to a first position a first aperture defines the narrow primary beam and when the second collimator is displaced to a second position the second aperture defines a wide radiation beam which irradiates an entire examination plane in the object.

9. A device as claimed in claim 3, further comprising:

a second collimator disposed between the radiation source and the object and means for displacing the second collimator perpendicular to the plane of examination, the second collimator defining two apertures and functioning so that when the second collimator is displaced to a first position a first aperture defines the narrow primary beam and when the second collimator is displaced to a second position the second aperture defines a wide radiation beam which irradiates an entire examination plane in the object.

* * * * *